(12) United States Patent
Coleman

(10) Patent No.: US 6,218,336 B1
(45) Date of Patent: Apr. 17, 2001

(54) ENHANCED HERBICIDES

(75) Inventor: Robert Coleman, Okemos, MI (US)

(73) Assignees: Applied CarboChemicals, Alto; Summerdale, Inc., Okemos, both of MI (US)

( * ) Notice: Subject to any disclaimer, the term of this patent is extended or adjusted under 35 U.S.C. 154(b) by 0 days.

(21) Appl. No.: 09/427,476

(22) Filed: Oct. 26, 1999

(51) Int. Cl.$^7$ .......................... A01N 63/00; A01N 59/00; A01N 37/00
(52) U.S. Cl. .......................... 504/118; 504/125; 504/142
(58) Field of Search .................................. 504/118, 125, 504/142

(56) References Cited

U.S. PATENT DOCUMENTS 5,035,741 * 7/1991 Puritch et al. .......................... 71/113
5,573,997 * 11/1996 Lojek et al. .......................... 504/142

FOREIGN PATENT DOCUMENTS

7157406 * 10/1993 (JP) .
9747199 * 12/1997 (WO) .

* cited by examiner

Primary Examiner—S. Mark Clardy
Assistant Examiner—Alton Pryor
(74) Attorney, Agent, or Firm—Pitney, Hardin, Kipp & Szuch LLP

(57) ABSTRACT

The invention provides, improved herbicide compositions, methods of making the compositions and methods of controlling plant growth. The subject invention relates to combining fatty acid based and other herbicides with succinic acid, succinic acid derivatives and other additives such as those having essentially no herbicidal activity to increase the activity of the herbicide and provide methods of controlling plant growth by applying a combination of a herbicidal fatty acid with succinic acid and/or succinic acid derivative chemicals and/or other additives. In addition to the use of succinic acid, combining other Krebs cycle acids with herbicides can also provide beneficial effects. Concentrations of herbicides and additives applied to plants in accordance with the invention can include compositions involving 0.1 to 30% herbicide, preferably 0.5 to 15% herbicide and additive and more preferably 1–8% herbicide. The ratio of herbicide, such as fatty acid herbicide to activity enhancing additives can be from 1:10 to 20:1, preferably 1:1 to 20:1, most preferably 1:1 to 5:1.

24 Claims, No Drawings

ENHANCED HERBICIDES

BACKGROUND OF THE INVENTION

The invention relates generally to herbicides, methods of improving existing herbicides and controlling the growth of plant life and more particularly to methods and products involving succinate-based chemicals and other additives which can enhance the activity (effectiveness) of herbicidal compounds. As used herein, herbicidal refers to materials which destroy or inhibit plant growth, such as by desiccation or defoliation for example, to act as a harvest aid or to control weed growth.

Glyphosate and paraquat are the number 1 and 2 non-selective herbicides used worldwide. Paraquat is extremely toxic and therefore unacceptable for many applications. Glyphosate can be slow acting, commonly requiring 1 to 2 weeks to achieve plant death and is therefore also unsuitable for many herbicide applications.

Other conventionally known herbicides include fatty acids, such as pelargonic acid, a nine carbon fatty acid, and caprylic acid, an eight carbon fatty acid. Scythe, sold by Mycogen/Dow and Liberty, made by AgrEvo are known commercially available herbicides. Pelargonic acid is the active ingredient in Scythe and glufosinate-ammonium is the active ingredient in Liberty. However, the activity of these products is such that the cost of products such as Scythe can be undesirably high and the amount of active ingredients needed in products such as paraquat could lead to undesirable effects.

Accordingly, it is desirable to provide improved herbicides, methods for enhancing the activity of existing herbicides and methods of controlling plant growth in order to overcome inadequacies of the prior art.

SUMMARY OF THE INVENTION

Generally speaking, in accordance with the invention, improved herbicide compositions, methods of making the compositions and methods of controlling plant growth are provided. The subject invention relates to combining fatty acid based and other herbicides with succinic acid, succinic acid derivatives and other additives such as those having essentially no herbicidal activity to increase the activity of the herbicide and provide methods of controlling plant growth by applying a combination of a herbicidal fatty acid with succinic acid and/or succinic acid derivative chemicals and/or other additives. In addition to the use of succinic acid, combining other Krebs cycle acids with herbicides can also provide beneficial effects. Concentrations of herbicides and additives applied to plants in accordance with the invention can include compositions involving about 0.1 to 30% herbicide and additive, preferably 0.5 to 15% herbicide and additive and more preferably 1–8% herbicide and additive. The ratio of herbicide, such as fatty acid herbicide to activity enhancing additive can be from about 1:10 to 20:1, preferably 1:1 to 20:1, more preferably 1:1 to 5:1.

Accordingly, it is an object of the invention to provide improved herbicidal compositions.

Another object of the invention is to provide additives which can enhance the activity of herbicidal compositions.

Yet another object of the invention is to improve the safety of herbicides.

A further object of the invention is to provide improved methods of plant control.

The invention accordingly comprises the several steps and the relation of one or more of such steps with respect to each of the others, and the compositions possessing the characteristics, properties and the relation of constituents useful to effect such steps, which will be exemplified in the compositions hereinafter described, all as exemplified in the following detailed disclosure, and the scope of the invention will be indicated in the claims.

DETAILED DESCRIPTION OF THE PREFERRED EMBODIMENTS

The invention is directed to improved herbicidal compositions. Herbicides, such as those including fatty acids as the active ingredient can be formulated at low fatty acid concentration and have relatively low herbicidal activity or at higher fatty acid concentration and have enhanced activity. However, it has been found that certain additives, such as organic acids and their derivatives, which may have substantially no herbicidal activity can enhance the herbicidal activity of herbicidal fatty acids and other herbicides and provide herbicides with either enhanced activity or reduced fatty acid concentrations. Preferred additives include those organic acids which are part of the Krebs cycle and in particular, succinic acid as well as succinic acid derivatives. Thus, substantially safe non-herbicidal additives are combined with G.R.A.S. (generally recognized as safe by the FDA) herbicidal compounds such as fatty acids, and the result is a generally safe herbicide with enhanced activity. As used herein, the term fatty acid will refer to aliphatic mono-carboxylic acids, including short chain mono-carboxylic acids such as acetic acid, unless indicated otherwise.

The following examples demonstrate the synergistic relationship between additives (such as succinic acid) and fatty acid herbicides such as caprylic acid, pelargonic acid and others. Other synergistic relationships between organic acids (for example, citric acid, tartaric acid, malic acid and lactic acid) with caprylic acid as the fatty acid were also exhibited. In general with the exception of tartaric acid, there was a general lack of correspondence between the acidity of the organic acid and the degree of synergy of the organic acid with caprylic acid. It was determined that tartaric acid (e.g. L-tartaric acid) exhibited particularly high performance enhancement of caprylic acid across a wide variety of plant types.

A synergistic relationship between succinic acid and sodium salicylate was also demonstrated where the effect of succinic acid alone on the plants treated was negligible.

Accordingly, it has been determined that combining certain organic acids and compounds having a significant herbicidal effect, such as pelargonic, caprylic, caproic, capric and oleic acid, and also such acids as acetic, butyric, valeric, hexanoic and heptanoic acid and compounds such as sodium salicylate, glyphosate (in Round Up) or glufosinate-ammonium with other organic acids and additives including those having substantially no herbicidal effect could enhance herbicidal activity and reduce costs, environmentally undesirable effects or be otherwise more convenient to use.

Effective additives include succinic acid and succinic acid derivatives such as dimethyl succinic acid, calcium succinate, magnesium succinate, diammonium succinate and ammonium succinate as well as certain other organic acids, such as tartaric acid, citric acid, malic acid, lactic acid, adipic acid and plant oils such as limonene and pine oil, especially Unipine (a pine oil derivative available from Busche, Boake & Allen, Inc.), as well as other additives including ammonium sulfate, ammonium tartrate, ammonium chloride and sodium salicylate.

In order to confirm that additives in accordance with the invention provided an enhanced herbicidal effect, a number of experiments were performed in which only fatty acids or other herbicides were applied to plants, the additives alone were applied and the fatty acids plus the additives were applied. The herbicides were applied in the "spray to drip" amount or at a calibrated 20–60 gallons/acre. "Spray to drip" is an uncalibrated application of fluid to foliage, where sufficient spray volume is used to sufficiently saturate the foliage surface until excess fluid begins to drip from the foliage. In general, about 5 to 200 gallons/acre, preferably 20–100 gallons/acre can be effective.

Fatty acids above 6–7 carbon atoms tend to be relatively insoluble in water. Caprylic and pelargonic acids are 8 and 9 carbon acids respectively and require a solvent, such as acetone or an emulsifier to help prevent separation between aqueous and lipid phases. Herbicides can be provided in concentrated form and then diluted at the point of use.

Aspects and embodiments of the invention will be described more clearly with reference to the following examples, which are intended to be interpreted as exemplary, and not in a limiting sense.

Example 1

Potato field trial: two varieties (Snowden and Russet Burbank)
Comparison of Desiccate II with experimental formulations

| | Average injury rating* & (% vine injury) (days after 1st application) | | | | | |
|---|---|---|---|---|---|---|
| | Snowden | | | Russet Burbank | | |
| Treatment: | Day 5 | Day 8 | Day 15 | Day 5 | Day 8 | Day 15 |
| 1  Desiccate II (2.175 quart/acre) | 0 (0) | 30 (10) | 100 (100) | 50 (40) | 60 (70) | 100 (96) |
| 2  4% pelargonic + 0.5% succinic acid | 90 (70) | 100 (94) | 100 (100) | 97 (90) | 98 (95) | 100 (100) |
| 3. 4% caprylic/capric + 0.5% succinic | 90 (70) | 96 (92) | 100 (100) | 95 (90) | 98(97) | 100 (100) |
| 4  4% caprylic/capric + 0.5% succinic + 1% sodium salicylate | 90 (80) | 100 (98) | 100 (100) | 95 (90) | 96 (92) | 100 (100) |
| 5  4% sodium salicylate + 0.5% succinic | 25 (0) | 40 (10) | 95 (90) | 70 (60) | 98 (92) | 100 (100) |
| 6  6% caprylic/capric + 0.5% succinic | 95 (75) | 100 (90) | 100 (100) | 80 (70) | 98 (94) | 100 (100) |

*Injury rating based on scale of 1–5, where 5 = complete desiccation of all plants/plot
Second application 5 days after 1st (application; each at 87 G/a (45 psi)
Treatment #1 contained 0.125% Wilfarm Crop Oil Concentrate
Treatments #2–4 and 6 contained 0.83% Emsorb 6900, 0.43% mineral oil and 1% Hasten
Treatment #5 contained 0.3% Sylgard 309
Summary: all experimental treatments (#2–6) better than treatment #1 (Desiccate II)

Example 2

Potato field trial: 2 applications of selected herbicides, including Desiccate II

| | | Injury rating*, average per plot | | | |
|---|---|---|---|---|---|
| Treatment | | Day 1 | Day 2 | Day 3 | Day 5 |
| 1  5% pelargonic | | 4.07 | 4 | 4.13 | 4.43 |
| 2  5% pelargonic + 1% di-ammonium succinate | | 4.23 | 4.23 | 4.47 | 4.57 |
| 3  5% caprylic/capric + 1% di-ammonium succinate | | 3.87 | 3.9 | 4.03 | 4.4 |
| 4  Desiccate II (1.5 quarts/acre) | | 1 | 1.5 | 1.67 | 3 |

*Injury rating, based on a scale of 1–5, where 5 = complete desiccation of all plants/plot
1% Hasten in treatments 1, 2 and 3. For treatment 4:0.125% Wilfarm Crop Oil Concentrate.
Treatments 1, 2 and 3 also had 0.86% Emsorb 6900 and 0.43% mineral oil
Plot size: 3 × 6 feet. Each treatment group had 3 replicates
40–42 G/acre, with <45 psi for 1st application and 45 psi for 2nd application
2nd treatment applied 2 days after 1st treatment
Variety: Katahdin (thick canopy), with active growth (irrigated)
Summary: 1) treatments 1–3 superior to treatment 4 (Desiccate II), 2) perlagonic acid enhanced by di-ammonium succinate Example 3

Dry bean (navy) field trial: single application of selected herbicides, including Desiccate II

| Treatment | Injury rating*, average per plot | | | | | % desiccation, day 14 | | |
|---|---|---|---|---|---|---|---|---|
| | Day 2 | Day 4 | Day 5 | Day 6 | Day 14 | foliage | vines | pod |
| 1  Desiccate II (1.5 quarts/acre) | 3.375 | 3.8 | 4.55 | 4.68 | 4.625 | 90 | 50 | 60 |
| 2  4% pelargonic + 0.5% succinic acid | 4.325 | 4.35 | 4.7 | 4.73 | 4.763 | 98 | 90 | 97 |
| 3  4% caprylic + 0.5% succinic acid | 4.413 | 4.43 | 4.76 | 4.83 | 4.8 | 98 | 90 | 97 |
| 4  4% sodium salicylate + 0.5% succinic | 4.388 | 4.38 | 4.68 | 4.73 | 4.775 | 95 | 80 | 97 |

*Injury rating, based on a scale of 1–5, where 5 = complete desiccation of all plants/plot
1% Hasten in treatments 2, 3 and 0.3% Sylgard 309 in treatment 4. Treatment 1 had 0.25% Wilfarm Crop Oil Concentrate
Treatments 2 and 3 also contained 0.86% Emsorb 6900 and 0.43% mineral oil
Plot size = 3 × 6 feet, with 4 replicates (plots) per treatment group
40 gallons per acre at 45 psi for one application
Dry bean variety (navy): Vista
Field
Summary: Treatments 2–4 were superior to treatment 1 (Desiccate II)

Example 4

Bean (black) trial: single application of selected herbicides, including Desiccate II

| Treatment: | Injury rating*, average per plot | | | | | % desiccation, day 19 | | |
|---|---|---|---|---|---|---|---|---|
| | Day 1 | Day 3 | Day 7 | Day 9 | Day 19 | foliage | vines | pods |
| 1  Desiccate II (1.5 quarts/acre) | 1.75 | 4.35 | 4.5 | 4.7 | 4.88 | 97 | 99 | 100 |
| 2  3% caprylic + 0.5% succinic acid | 4.3 | 4.55 | 4.55 | 4.7 | 4.9 | 99 | 99 | 100 |
| 3  3% pelargonic + 0.5% succinic acid | 4.55 | 4.75 | 4.78 | 4.85 | 5 | 100 | 100 | 100 |
| 4  3% sodium salicylate + 0.5% succinic acid | 45 | 4.7 | 4.7 | 4.83 | 5 | 100 | 100 | 100 |

*Injury rating, based on a scale of 1–5, where 5 = complete desiccation of all plants/plot
1% Hastern in treatments 2, 3 and 0.3% Sylgard 309 in treatment 4. Treatment 1 had 0.125% Wilfarm Crop Oil Concentrate
Treatment 2 and 3 also contained 0.86% Emsorb 6900 and 0.43% mineral oil
Plot size: 3 × 6 feet, with 2 replicates (plots) per treatment group
40 gallons per acre at 45 psi for one application
Dry bean variety: black, T39
Field
Summary: Treatments 2–4 superior to treatment 1

Example 5

Synergistic interactions of succinic acid and di-ammonium succinate with herbicidal compounds, on navy dry beans

| Treatment: | Injury rating*, average per plot | | | | | % desiccation (Day 12) | | |
|---|---|---|---|---|---|---|---|---|
| | Day 1 | Day 2 | Day 3 | Day 4 | Day 12 | foliage | vines | pods |
| 1  3% caprylic | 3.5 | 3.93 | 3.93 | 4 | 4.2 | 50 | 10 | 80 |
| 2  3% caprylic + 0.5% succinic acid | 4.43 | 4.43 | 4.6 | 4.5 | 4.7 | 95 | 70 | 85 |
| 3  3% caprylic + 2% succinic acid | 4.5 | 4.47 | 4.57 | 4.5 | 4.8 | 99 | 85 | 90 |
| 4  3% caprylic + 2.52% di-ammonium succinate | 4.47 | 4.43 | 4.67 | 4.6 | 4.8 | 99 | 90 | 99 |
| 5  3% sodium salicylate | 3.8 | 4.13 | 4.57 | 4.5 | 4.7 | 92 | 70 | 90 |
| 6  3% sodium salicylate + 0.5% succinic acid | 3.93 | 4.27 | 4.63 | 4.6 | 4.8 | 95 | 85 | 92 |
| 7  3% sodium salicylate + 2% succinic acid | 4.2 | 4.4 | 4.67 | 4.6 | 4.9 | 97 | 80 | 95 |
| 8  3% sodium salicylate + 2.52% di-ammonium succinate | 4.4 | 4.43 | 4.72 | 4.6 | 4.9 | 97 | 90 | 95 |
| 9  0.5% succinic acid | 0 | 0 | 0 | 0 | 0 | 0 | 0 | 0 |
| 10  2% succinic acid | 0 | 0 | 0 | 0 | 0 | 0 | 0 | 0 |
| 11  2.52% di-ammonium succinate | 0 | 0 | 0 | 0 | 0 | 0 | 0 | 0 |
| 12  0.5% succinic acid | 0 | 0 | 0 | 0 | 0 | 0 | 0 | 0 |

-continued

Synergistic interactions of succinic acid and di-ammonium succinate
with herbicidal compounds, on navy dry beans

| Treatment: | Injury rating*, average per plot | | | | | % desiccation (Day 12) | | |
|---|---|---|---|---|---|---|---|---|
| | Day 1 | Day 2 | Day 3 | Day 4 | Day 12 | foliage | vines | pods |
| 13  2% succinic acid | 0 | 0 | 0 | 0 | 0 | 0 | 0 | 0 |
| 14  2.52% di-ammonium succinate | 0 | 0 | 0 | 0 | 0 | 0 | 0 | 0 |

*Injury rating, based on a scale of 1–5, where 5 = complete desiccation of all plants/plot
Treatments 1–4, 9–11: each in 0.86% Emsorb 6900, 0.43% mineral oil, 1% Hasten
Treatments 5–8, 12–14: each in 0.3% Sylgard 309
Succinic (2%) and di-ammonium succinate (2.52%) are equimolar
Plot size: 3 × 6 feet. Each treatment group had 3 replicates
One application at 40 G/acre, 45 psi
Variety: dry bean (navy Vista)
Field
Summary: both succinic acid and di-ammonium succinate were synergistic with sodium salicylate and caprylic acid

Example 6

Synergistic interactions of succinic acid and di-ammonium succinate
with other herbicidal compounds, on dry beans (black)

| Treatment: | Injury rating*, average per plot | | % desiccation (Day 12) | | |
|---|---|---|---|---|---|
| | Day 2 | Day 12 | foliage | vines | pods |
| 1   3% caprylic | 4 | 4.73 | 80 | 92 | 95 |
| 2   3% caprylic + 0.5% succinic acid | 4.37 | 4.87 | 97 | 95–98 | 90 |
| 3   3% caprylic + 2% succinic acid | 4.43 | 4.92 | 99 | 98 | 97 |
| 4   3% caprylic + 2.52% di-ammonium succinate | 4.37 | 4.9 | 99 | 95–97 | 85 |
| 5   3% sodium salicylate | 4 | 4.78 | 95 | 90 | 90 |
| 6   3% sodium salicylate + 0.5% succinic acid | 4.23 | 4.87 | 99 | 98 | 92 |
| 7   3% sodium salicylate + 2% succinic acid | 4.07 | 4.88 | 99 | 95 | 90 |
| 8   3% sodium salicylate + 2.52% di-ammonium succinate | 4.37 | 4.8 | 99 | 92 | 80 |
| 9   0.5% succinic acid | 0 | 0 | 0 | 0 | 0 |
| 10  2% succinic acid | 0 | 0 | 0 | 0 | 0 |
| 11  2.52% di-ammonium succinate | 0 | 0 | 0 | 0 | 0 |
| 12  0.5% succinic acid | 0 | 0 | 0 | 0 | 0 |
| 13  2% succinic acid | 0 | 0 | 0 | 0 | 0 |
| 14  2.52% di-ammonium succinate | 0 | 0 | 0 | 0 | 0 |

*Injury rating, based on a scale of 1–5, where 5 = complete desiccation of all plants/plot
Treatments 1–4, 9–11: each in 0.86% Emsorb 6900, 0.43% mineral oil, 1% Hasten
Treatments 5–8, 12–14: each in 0.3% Sylgard 309
Succinic (2%) and di-ammonium succinate (2.52%) are equimolar
Plot size: 3 × 6 feet. Each treatment group had 3 replicates
One application at 40 G/acre, 45 psi
Variety: black beans (dry bean variety T39)
Summary: both succinic acid and di-ammonium succinate were synergistic with sodium salicylate and caprylic acid

Example 7

Enhancement of caprylic acid/sodium salicylate as an herbicide, by succinic acid

| | Treatment | Succinic acid (%) | Relative injury rating* (average, based on 2 ratings) potatoes | All plants |
|---|---|---|---|---|
| 1 | 0.25% caprylic + 0.25% sodium salicylate | 0 | 3 | 8.5 |
| 2 | 0.25% caprylic + 0.25% sodium salicylate | 0.5 | 5 | 17 |
| 3 | 0.25% caprylic + 0.25% sodium salicylate | 1 | 6 | 17.6 |
| 4 | 0.25% caprylic + 0.25% sodium salicylate | 1.5 | 7.7 | 19.7 |
| 5 | 0.25% caprylic + 0.25% sodium salicylate | 2 | 6.8 | 18.9 |
| 6 | 0.5% caprylic + 0.5% sodium salicylate | 0 | 4.8 | 15.1 |
| 7 | 0.5% caprylic + 0.5% sodium salicylate | 0.5 | 5.3 | 17.7 |
| 8 | 0.5% caprylic + 0.5% sodium salicylate | 1 | 5.5 | 19.7 |
| 9 | 0.5% caprylic + 0.5% sodium salicylate | 1.5 | 7 | 21.3 |
| 10 | 0.5% caprylic + 0.5% sodium salicylate | 2 | 7.5 | 22.1 |

*A rating of 1–5 given (5 = complete desiccation of all plants), for each treatment (1–2 plants/pot)
Two independent evaluations (ratings) performed
Helena Kinetic at 0.2% used for all treatments
All formulations in 30% acetone
Spray to drip applications to dry beans, snapbeans and potato plants

Example 8

Effect of 1% succinic acid on herbicidal activity of Liberty and Scythe

| Treatment | Total score for all injury ratings* |
|---|---|
| 1 4% Scythe | 66 |
| 2 2% Scythe | 54.2 |
| 3 2% Scythe + 1% succinic | 56.1 |
| 4 2% Scythe + 0.25% caprylic + 0.25% sodium salicylate | 56.3 |
| 5 2% Scythe + 0.25% caprylic + 0.25% sodium salicylate + 1% succinic | 60.3 |
| 6 2% Scythe + 0.5% sodium salicylate | 47.5 |
| 7 Liberty (4 oz/gal) | 87.8 |
| 8 Liberty (2 oz/gal) | 76.6 |
| 9 Liberty (2 oz/gal) + 1% succinic | 81 |
| 10 Liberty (2 oz/gal) + 0.25% caprylic + 0.25% sodium salicylate | 77 |
| 11 Liberty (2 oz/gal) + 0.25% caprylic + 0.25% sodium salicylate + 1% succinic | 78.4 |
| 12 Liberty (2 oz/gal) + 0.5% sodium salicylate | 75.7 |
| 13 Liberty (1 oz/gal) | 65.9 |
| 14 Liberty (1 oz/gal) + 1% succinic | 70.3 |
| 15 Liberty (1 oz/gal) + 0.25% caprylic + 0.25% sodium salicylate | 67.6 |
| 16 Liberty (1 oz/gal) + 0.25% caprylic + 0.25% sodium salicylate + 1% succinic | 72.1 |
| 17 Liberty (1 oz/gal) + 0.5% sodium salicylate | 70.8 |

*Injury rating based on 1 to 6, where 6 = complete desiccation of plant.
Six independent evaluations performed and all scores, based on ratings for nutsedge, snapbeans and Kentucky bluegrass, where given as a total score for each treatment Kinetic at 0.2% used for all treatments. Applications of treatments made via sprayto drip. Snapbeans (full bean production), nutsedge (6–8 inches, height) and bluegrass (blade height 3 inches)
1% succinic acid = zero rating. Succinic was synergistic with those combinations given above.

Example 9

Enhancement of RoundUp Ultra's herbicidal activity on snapbeans and potatoes using 1% succinic acid

| Treatment | Average injury rating* potatoes | snapbeans |
|---|---|---|
| 1 RoundUp Ultra, 1.25% | 4.48 | 2.92 |
| 2 RoundUp Ultra, 1.25% + 1% succinic acid | 4.67 | 4.78 |
| 3 RoundUp Ultra, 0.25% | 3.35 | 2.82 |
| 4 RoundUp Ultra, 0.25% + 1% succinic acid | 4.37 | 3.2 |

*Rating of 1 to 6 = complete desiccation
Average rating based on 6 independent evaluations of injury to plants
Application rate of 1.25% RoundUp Ultra at 40 G/acre = 2 quarts/acre (0.25% RoundUp Ultra at 40 G/acre = 0.4 quarts/acre)
Mature snapbeans (with beans pods) and potatoes at 6–8 inches in height were used
Summary: succinic acid synergistic with RoundUp

Example 10

Succinic acid enhancement of herbicidal activities: sodium salicylate +/− caprylic acid

| | Treatment | Injury rating* Spray to drip | Average rating per pot |
|---|---|---|---|
| 1 | 0.75% caprylic + 0.75% sodium salicylate | 45.1 | 2.82 |
| 2 | 0.75% caprylic + 0.75% sodium salicylate + 1% succinic acid | 60.3 | 3.77 |
| 3 | 1% caprylic + 1% sodium salicylate | 50.1 | 3.13 |
| 4 | 1% caprylic + 1% sodium salicylate + 1% succinic acid | 61.1 | 3.82 |
| 5 | 1.5% sodium salicylate | 56.2 | 3.51 |
| 6 | 1.5% sodium salicylate + 1% succinic acid | 62.5 | 3.91 |

*For each pot, a rating (1 to 5) was given, where 5 was complete desiccation of all plants
Three independent evaluations were done
Test plants for spray to drip application: Kentucky bluegrass, velvetleaf, foxtail, tomato, potato and snapbeans
All spray solutions contained 30% acetone and 0.3% Sylgard 309
Caprylic acid was v/v and succinic acid and sodium salicylate were at wt/v
Summary: Succinic acid enhanced effectiveness

Example 11

Enhancement of herbicide formulations with 1% succinic acid

| Treatment | | | | Average injury rating |
|---|---|---|---|---|
| 1 | 0.5% caprylic + 0.5% sodium salicylate | | | 31.6 |
| 2 | 0.5% caprylic + 0.5% sodium salicylate 0.5% ammonium sulfate | | | 41.4 |
| 3 | 0.5% caprylic + 0.5% sodium salicylate 0.5% ammonium sulfate | 0.5% ammonium chloride | | 41.6 |
| 4 | 0.5% caprylic + 0.5% sodium salicylate 0.5% ammonium chloride | | | 39.2 |
| 5 | 0.5% caprylic + 0.5% sodium salicylate 0.5% ammonium sulfate | | 1% succinic acid | 46.8 |
| 6 | 0.5% caprylic + 0.5% sodium salicylate 0.5% ammonium sulfate | 0.5% ammonium chloride | 1% succinic acid | 44.6 |
| 7 | 0.5% caprylic + 0.5% sodium salicylate 0.5% ammonium chloride | | 1% succinic acid | 43.6 |
| 8 | 0.5% caprylic + 0.5% sodium salicylate 1% succinic acid | | | 40 |

*A rating of 1–5, where 5 = complete desiccation of all plants
Three independent evaluations (ratings) performed
Helena Kinetic at 0.1% used for all applications
All formulations in 30% acetone
Spray to drip applications to snapbeans and potato plants

Example 12

Succinic acid enhancement of herbicidal activities: sodium salicylate combined with hexanoic, acetic or caprylic/capfic acid

| | Treatment | Injury rating* | |
|---|---|---|---|
| | | Spray to drip | Average rating per pot |
| 1 | 2% hexanoic + 1% sodium salicylate | 44.1 | 3.68 |
| 2 | 2% hexanoic + 1% sodium salicylate + 1% succinic | 55.8 | 4.65 |
| 3 | 3% acetic + 1% sodium salicylate | 47.1 | 3.93 |
| 4 | 3% acetic + 1% sodium salicylate + 1% succinic | 54.4 | 4.53 |
| 5 | 2% caprylic/capric + 1% sodium salicylate | 50 | 4.17 |
| 6 | 2% caprylic/capric + 1% sodium salicylate + 1% succinic | 54.4 | 4.53 |
| 7 | 2% caprylic/capric + 1% sodium salicylate + 2% succinic | 56.7 | 4.73 |

*For each pot, a rating (1 to 5) was given, where 5 was complete desiccation of all plants
Two independent evaluations were done
Test plants for spray to drip application: velvetleaf, corn snapbeans, foxtail and tomatoes
All spray solutions contained 30% acetone and 0.3% Sylgard 309
Acetic, hexanoic and caprylic/capric acid were v/v and succinic acid was wt/v
Caprylic/capric (caprylic, capric, caproic and lauric at 58, 40, 1 and 1%, respectively).

Example 13

Succinic acid enhancement of oleic acid/sodium salicylate herbicidal activity

| | Treatment | Injury rating* | |
|---|---|---|---|
| | | Spray to drip | Average rating per pot |
| 1 | 2% oleic acid | 26.4 | 2.2 |
| 2 | 2% oleic acid + 1% sodium salicylate | 37.9 | 3.16 |
| 3 | 2% oleic acid + 1% sodium salicytate + 1% succinic acid | 49.2 | 4.1 |
| 4 | 2% oleic acid + 1% succinic acid | 28.1 | 2.33 |

*For each pot, a rating (1 to 5) was given, where 5 was complete desiccation of all plants
Two independent evaiuations were done
Test plants for spray to drip: lambsquarter, velvetleaf, foxtail, nutsedge and potatoes
All spray solutions contained 50% acetone and 0.3% Sylgard 309
Oleic acid was v/v and succinic acid and sodium salicylate was wt/v
Summary: Sodium salicylate and succinic acid enhance effectiveness

Example 14

Succinic acid enhancement of oleic acid/sodium salicylate herbicidal activity

| | Treatment | Total Injury rating* | | | |
|---|---|---|---|---|---|
| | | 60 G/a | Spray to drip | Total | Average rating per pot |
| 1 | 2% oleic acid | 23.5 | 22.3 | 45.8 | 1.91 |
| 2 | 2% oleic acid + 1% sodium salicylate | 52.3 | 34.7 | 87 | 3.63 |
| 3 | 2% oleic acid + 1% sodium salicylate + 1% succinic acid | 63.8 | 37.1 | 101 | 4.2 |

*For each pot, a rating (1 to 5) was given, where 5 was complete desiccation of all plants
Both 60 gallons/acre and spray to drip applications were made.
Two independent evaluations for both 60 G/a and spray to drip applications
Test plants for 60 G/a: lambsquarter, foxtail and velvetleaf
Test plants for spray to drip: snapbeans, com and tomatoes
All spray solutions contained 50% acetone and 0.3% Sylgard 309
Oleic acid was v/v and succinic acid and sodium salicylate was wt/v

Example 15

Cotton desiccation: comparison of Scythe with formulations containing caprylic/capric, sodium salicylate and succinic acid

| Treatment | | | | Average rating* Three evaluations | | | Average rating for all 3 evaluations |
|---|---|---|---|---|---|---|---|
| | | | | 1 | 2 | 3 | |
| 1 | 2% caprylic + 1% sodium salicylate | 1% succinic acid | 0.3% Sylgard 309 | 4 | 3.5 | 3.6 | 3.7 |
| 2 | 2% caprylic + 1% sodium salicylate | 1% succinic acid | 0.3% Hasten | 3.8 | 4.1 | 4 | 3.97 |
| 3 | 2% caprylic + 1% sodium salicylate | 1% succinic acid | 0.3% Hasten | 4.2 | 4.5 | 4.4 | 4.4 |
| 4 | 2% Scythe (1.2% active ingredients) | | | 2 | 2 | 2 | 2 |
| 5 | 4% Scythe (2.4% active ingredients) | | | 3.4 | 3.2 | 3.3 | 3.27 |

*rating based on visual injury rating of 1–5, where 5 = complete desiccation of cotton foliage
Cotton variety = DeltaPine NuCotn 33-b
All treatments (except Scythe) in 30% acetone
Caprylic, capric, caproic and lauric at 58, 40, 1 and 1%, respectively; i.e.
Henkel's Emery 658, used at v/v, in water
Applications at 60 gallons/acre

Example 16

Herbicide activity of caprylic acid/sodium salicylate +/- succinic acid

| | Treatment | Total injury rating* |
|---|---|---|
| 1 | 1% caprylic + 3% sodium salicylate + 0.5% succinic | 97.7 |
| 2 | 3% caprylic + 1% sodium salicylate + 0.5% succinic | 97.9 |
| 3 | 1% caprylic + 3% sodium salicylate + 1.5% succinic | 97.9 |
| 4 | 3% caprylic + 1% sodium salicylate + 1.5% succinic | 99.9 |
| 5 | 1% caprylic + 3% sodium salicylate | 79.8 |
| 6 | 3% caprylic + 1% sodium salicylate | 91.3 |

*For each pot, a rating (1 to 5) was given, where 5 was complete desiccation of all plants
Both 60 gallons/acre and spray to drip applications were made.
Two independent evaluations for both 60 G/a and spray to drip applications
Test plants for 60 G/a: lambsquarter, foxtail and Kentucky bluegrass
Test plants for spray to drip: nutsedge, foxtail and velvetleaf
All spray solutions contained 30% acetone and 0.3% Hasten
Caprylic acid was v/v and succinic acid and sodium salicylate were wt/v

Example 17

Herbicidal activity of caproic acid with other compounds: succinic acid and sodium salicylate

| | | Total injury ratings* | | |
|---|---|---|---|---|
| | Treatment | 60 G/a | Spray to drip | Total score |
| 1 | 2% caproic | 11.2 | 7.3 | 18.5 |
| 2 | 2% caproic + 1% succinic | 13.8 | 7.6 | 21.4 |
| 3 | 2% caproic + 2% succinic | 12.7 | 7.1 | 19.8 |
| 4 | 3% caproic | 13.9 | 7 | 20.9 |
| 5 | 3% caproic + 1% succinic | 14.1 | 7.9 | 22 |
| 6 | 3% caproic + 2% succinic | 14.5 | 8.2 | 22.7 |
| 7 | 2% caproic + 1% sodium salicylate | 13.5 | 8.7 | 22.2 |
| 8 | 2% caproic + 1% sodium salicylate + 1% succinic | 16.7 | 9.2 | 25.9 |

*For 60 G/a: 4 pots/treatment, testing lambsquarter, pigweed and velvetleaf
*For spray to drip: 2 pots/treatment, testing lambsquarter and foxtail
For each pot (2–20 plants/pot), a rating of 1–5 given, where 5 was complete desiccation of all plants
All solutions included 1% Emsorb 6900 and 0.3% Hasten
Summary: sodium salicylate and succinic acid enhance effectiveness

Example 18

Herbicidal activity of caprylic acid combined with other compounds (i.e. salts of succinate +/- sodium salicate)

| | | Total injury ratings* | | |
|---|---|---|---|---|
| | Treatment | 60 G/a | Spray to drip | Total score |
| 1 | 2% caprylic | 61 | 8.2 | 69.2 |
| 2 | 2% caprylic + 1.5% diammonium succinate | 67.9 | 8.8 | 76.7 |
| 3 | 2% caprylic + 1.5% potassium succinate | 58 | 7.6 | 65.6 |
| 4 | 2% caprylic + 1.5% sodium salicylate | 63.7 | 7.8 | 71.5 |
| 5 | 2% caprylic + 1.5% sodium salicylate + 1.5% diammonium succinate | 70 | 8.6 | 78.6 |
| 6 | 2% caprylic + 1.5% sodium salicylate + 1.5% potassium succinate | 58.9 | 7.5 | 66.4 |

*For 60 G/a: 8 total pots/treatment, testing lambsquarter, pigweed, velvetleaf and foxtail
*For spray to drip: 2 total pots/treatment, testing velvetleaf and foxtail
Evaluations made: 2 for plants treated at 60 G/a and 1 evaluation for "spray to drip"

-continued

Herbicidal activity of caprylic acid combined with other compounds
(i.e. salts of succinate +/− sodium salicate)

| Treatment | Total injury ratings* | | |
|---|---|---|---|
| | 60 G/a | Spray to drip | Total score |

For each pot (2–20 plants/pot), a rating of 1–5 given, where 5 was complete desiccation of all plants
All treatments included 1% Emsorb 6900

Example 19

Efficacy of caprylic with succinic or ammonium succinate, as herbicides in an emulsilication system (Emsorb 6900)

| | | Injury rating*, total score for 2 evaluations | | | |
|---|---|---|---|---|---|
| | Treatment | 60 G/a | Spray to drip | Total Rating | Average rating per pot |
| 1 | 2% caprylic | 73.6 | 49.8 | 123.4 | 4.11 |
| 2 | 2% caprylic + 1.5% ammonium succinate | 76.1 | 54.5 | 130.6 | 4.35 |
| 3 | 2% caprylic + 3% ammonium succinate | 76.4 | 57.7 | 134.1 | 4.47 |
| 4 | 2% caprylic + 1.5% succinic acid | 80.6 | 52.4 | ? 33 | 4.43 |

*For each pot, a rating (1 to 5) was given, where 5 was complete desiccation of all plants
Two independent evaluations done for both 60 G/a and spray to drip
Test plants for 60 G/a: black nightshade, redroot pigweed, lambsquarter, foxtail, velvetleaf and snapbeans
Test plants for spray to drip: redroot pigweed, lambsquarter, velvetleaf and foxtail
All spray solutions contained 1% Emsorb (Henkel) and 0.3% Hasten
Caprylic acid was at v/v and succinic acid and ammonium succinate were at wt/v

Example 20

Efficacy of caprylic with succinic or ammonium succinate, as herbicides in an emulsilication system (Emsorb 6900)

| | | Injury rating*, total score for 2 evaluations | | | |
|---|---|---|---|---|---|
| | Treatment | 60 G/a | Spray to drip | Total Rating | Average rating per pot |
| 1 | 3% caprylic | 142 | 36.6 | 178.4 | 4.05 |
| 2 | 3% caprylic + 0.5% ammonium succinate | 145 | 37.5 | 182.2 | 4.14 |
| 3 | 3% caprylic + 1.5% ammonium succinate | 145 | 39.8 | 185 | 4.2 |
| 4 | 3% caprylic + 1.5% succinic acid | 151 | 44.6 | 195.9 | 4.45 |

*For each pot, a rating (1 to 5) was given, where 5 was complete desiccation of all plants
Two independent evaluations done for both 60 G/a and spray to drip
Test plants for 60 G/a: black nightshade, redroot pigweed, foxtail, lambsquarter and snapbeans
Test plants for spray to drip: redroot pigweed, velvetleaf, nutsedge and foxtail
All spray solutions contained 1% emsorb (Henkel) and 0.3% Hasten
Caprylic acid was at v/v and succinic acid and ammonium succinate were at wt/v

Example 21

Efficacy of 1.5% succinic acid with oleic, caprylic or pelargonic acid, as herbicides in an emulsification system (Emsorb 6900)

| | | Injury rating*, total score for 2 evaluations | | | |
|---|---|---|---|---|---|
| | Treatment | 60 G/a | Spray to drip | Total Rating | Average rating per pot |
| 1 | 3% oleic | 24.2 | 9.4 | 33.6 | 1.2 |
| 2 | 3% oleic + 1.5% succinic | 27.3 | 8.7 | 36 | 1.29 |
| 3 | 3% caprylic | 88.1 | 35.4 | 123.5 | 4.41 |
| 4 | 3% caprylic + 1.5% succinic | 91.5 | 37.5 | 129 | 4.61 |
| 5 | 3% pelargonic | 85.3 | 37.6 | 122.9 | 4.39 |
| 6 | 3% pelargonic + 1.5% succinic | 91.2 | 37.4 | 128.6 | 4.59 |

*For each pot, a rating (1 to 5) was given, where 5 was complete desiccation of all plants
Two independent evaluations done for both 60 G/a and spray to drip
Test plants for 60 G/a: velvetleaf, black nightshade, redroot pigweed, foxtail and snapbeans
Test plants for spray to drip: black nightshade, velvetleaf, foxtail and snapbeans
All spray solutions contained 1% Emsorb (Henkel) and 0.3% Hasten
Oleic, caprylic and pelargonic at v/v and succinic acid at wt/v
Succinic acid, alone, had a rating of zero. Succinic acid was synergistic with oleic, caprylic and pelargonic acids

Example 22

Efficacy of caprylic + sodium salicylate + succinic acid, as an herbicide in an emulsification system (Emsorb 6900)

| | | Injury rating*, total score for 2 evaluations | | | |
|---|---|---|---|---|---|
| | Treatment | 60 G/a | Spray to drip | Total Rating | Average rating per pot |
| 1 | 2% caprylic + 1.5% succinic | 58.5 | 62 | 120.5 | 3.08 |
| 2 | 2% caprylic + 1.5% succinic + 1% sodium salicylate | 65 | 64.1 | 129.1 | 3.31 |
| 3 | 3% caprylic + 1.5% succinic | 68.7 | 68.1 | 136.8 | 3.51 |
| 4 | 3% caprylic + 1.5% succinic + 1% sodium salicylate | 72 | 71.1 | 143.1 | 3.67 |
| 5 | 4% caprylic + 1.5% succinic | 71 | 66.6 | 137.6 | 3.53 |

*For each pot, a rating (1 to 5) was given, where 5 was complete desiccation of all plants
Two independent evaluations done for both 60 G/a and spray to drip
Test plants for 60 G/a: redroot pigweed, velvetleaf, snapbeans, cotton and potatoes
Test plants for spray to drip: black nightshade, lambsquarter, foxtail and snapbeans
All spray solutions contained 1% Emsorb (Henkel) and 0.3% Hasten
Caprylic acid was at v/v and succinic acid and sodium salicylate were at wt/v
Succinic acid, alone, had a rating of zero. Succinic acid was synergistic with oleic, caprylic and pelargonic acids

Example 23

Herbicidal activity: relationships between caprylic acid and succinic acid +/− ammonium sulfate

| | | Injury rating*, total score for 2 evaluations | | | |
|---|---|---|---|---|---|
| | Treatment | 60 G/a | Spray to drip | Total Rating | Average rating per pot |
| 1 | 4% caprylic acid | 60.7 | 56.1 | 116.8 | 4.49 |
| 2 | 4% caprylic acid + 0.5% succinic acid | 63.9 | 57 | 120.9 | 4.65 |
| 3 | 4% caprylic acid + 1% succinic acid | 61.6 | 55.6 | 117.2 | 4.51 |
| 4 | 4% caprylic acid + 2% succinic acid | 59.4 | 57.4 | 116.8 | 4.49 |
| 5 | 4% caprylic acid + 0.5% succinic acid + ammonium sulfate | 60.4 | 56.6 | 117 | 4.5 |
| 6 | 4% caprylic acid + 1% succinic acid + ammonium sulfate | 64 | 57.8 | 121.8 | 4.68 |
| 7 | 4% caprylic acid + 2% succinic acid + ammonium sulfate | 62.1 | 57.4 | 119.5 | 4.6 |

*For 60 G/a: 7 total pots/treatment, testing redroot pigweed, foxtail and velvetleaf
For spray to drip: 6 total pots/treatment, testing foxtail, dry beans and pigweed
For each pot (2–20 plants/pot), a rating of 1 to 5 given, where 5 was complete desiccation of all plants
Two independent evaluations (ratings) done for plants treated at both 60 G/a and spray to drip
All treatments included Emsorb 6900 (Henkel) at 1%
Caprylic acid and succinic acid, as v/v and wt/v, respectively, in water
Succinic acid, alone, had a rating of zero. Caprylic acid + succinic acid was synergistic

Example 24

Herbicidal activity: comparison of fatty acids, when combined with succinic acid and sodium salicylate

| | | | Total Injury ratings, combined, for two separate evaluations* | | | |
|---|---|---|---|---|---|---|
| | Treatment | pH, spray solution | 60 G/a | Spray to drip | Total | Average rating/pot |
| 1 | 3% butyric acid + succinic/NaSal | 3.8 | 102.3 | 52.5 | 154.8 | 4.3 |
| 2 | 3% valeric acid + succinic/NaSal | 3.9 | 105 | 53.8 | 158.8 | 4.41 |
| 3 | 3% caproic acid + succinic/NaSal | 4.4 | 104.9 | 51.9 | 156.8 | 4.36 |
| 4 | 3% heptanoic acid + succinic/NaSal | 4.5 | 108.9 | 54.1 | 163 | 4.53 |
| 5 | 3% caprylic acid + succinic/NaSal | 4.5 | 112.4 | 55.5 | 167.9 | 4.67 |
| 6 | 3% pelargonic acid + succinic/NaSal | 4.5 | 111.9 | 56.6 | 168.5 | 4.68 |
| 7 | 3% oleic acid + succinic/NaSal | 4.5 | 105 | 53.2 | 158.2 | 4.39 |
| 8 | 3% caprylic/capric + succinic/NaSal | 4.6 | 114.3 | 57.3 | 171.6 | 4.77 |

*For 60 G/a: 12 total pots/treatment, testing redroot pigweed, wheat, foxtail and velvetleaf
For spray to drip: 6 total pots/treatment, testing redroot pigweed, foxtail and velvetleaf Herbicidal activity: comparison of fatty acids, when combined with succinic acid and sodium salicylate For each pot (2–20 plants/pot), a rating of 1 to 5 given, where 5 was complete desiccation of all plants
Two independent evaluations (ratings) done for plants treated at both 60 G/a and spray to drip
All treatments included 0.3% Hasten
Fatty acids at v/v and succinic acid (1%) and sodium salicylate (1%) at wt/v, in water
Caprylic/capric: caprylic, capric, caproic and lauric at 58, 40, 1 and 1% respectively (per Henkel Corporation)
No apparent correlation between pH of spray solutions (including Hasten) and herbicidal activity.

Example 25

Synergistic relationships between 5% caprylic/capric (c/c) and succinic acid: desiccation of cotton plants

| Average Rating | Average percent of foliage desiccated | Treatment | | |
|---|---|---|---|---|
| 2 | 20 | | | 5% c/c |
| 4 | 70 | 0.5% succinic | and | 5% c/c |
| 4 | 60 | 1% succinic | and | 5% c/c |
| 4 | 70 | 2% succinic | and | 5% c/c |

*Average rating based on 1–5, where 5 = complete desiccation of foliage
Test plant: DeltaPine NuCotn 33-b, open boll
c/c = Caprylic, capric, caproic and lauric at 58, 40, 1 and 1%, respectively; i.e., Henkel's Emery 658, used at v/v, in water
All treatments contained 1% Emsorb 6900
Treatment of plants with succinic acid, alone, had a rating of zero
caprylic/capric and succinic at these concentrations were synergistic

Example 26

Synergistic relationships between 5% caprylic/capric (c/c) and succinic acid

Average rating: degree of plant damage
(1–5, where 5 = complete desiccation)

| 60 G/acre | Spray to drip | Treatment Ingredients | | |
|---|---|---|---|---|
| 4.14 | 4.61 | | | 5% c/c |
| 4.33 | 4.83 | 0.5% succinic | and | 5% c/c |
| 4.43 | 4.82 | 1% succinic | and | 5% c/c |
| 4.41 | 4.71 | 2% succinic | and | 5% c/c |

Test plants: cotton (DelataPine NuCotn 33b), potatoes (Snowden), pigweed, sudan grass, wheat, foxtail, dry beans and velvetleaf
c/c - Caprylic, capric, caproic and lauric at 58, 40, 1 and 1%, respectively; i.e., Henkel's Emery 658, used at v/v, in water
All treatments contained 1% Emsorb 6900
Treatment of plants with succinic acid, alone, had a rating of zero
Caprylic/capric (c/c) and succinic acid were synergistic

Example 27

Synergistic relationship between caprylic/capric (c/c) and succinic acid, as harvest aids for potatoes and cotton Average rating: degree of plant damage
(1–5, where 5 = complete desiccation)
Average, 2 evaluations

| Cotton | Potatoes | Treatment Ingredients |
|---|---|---|
| 3.75 | 4.1  |                       8% c/c |
| 4.35 | 4.25 | 0.5% succinic and 8% c/c |
| 4.65 | 4.15 | 1% succinic   and 8% c/c |
| 4.65 | 4.35 | 2% succinic   and 8% c/c |

Cotton (DeltaPine NuCotn 33b) and potatoes (Snowden) were at full maturity
Application volume/acre was 40 G/a
C/C = Caprylic, capric, caproic and lauric at 58, 40, 1 and 1 %, respectively; i.e., Henkel's Emery 658, used at v/v, in water
Treatment of plants with succinic acid, alone, had a rating of zero
Caprylic/capric (c/c) and succinic acid is synergistic

Example 28

Herbicidal activities: synergy between succinic acid and pelargonic acid

| Treatment | Total injury ratings* | | Spray to drip | Total |
|---|---|---|---|---|
|  | 40 G/a | 60 G/a |  |  |
| 1  4% pelargonic acid | 41.6 | 45.6 | 66.2 | 153.4 |
| 2  4% pelargonic acid + 0.5% succinic acid | 42.8 | 46.7 | 66.3 | 155.8 |
| 3  0.5% succinic acid | 0 | 0 | 0 | 0 |

*For 40 G/a: 9 total pots/treatment, testing crab grass, pigweed, chick weed and foxtail
*for 60 G/a: 10 total pots/treatment, testing pigweed, Kentucky bluegrass, foxtail, crab grass and barnyard grass
*For spray to drip: 7 total pots/treatment, testing Kentucky bluegrass, pigweed, barnyard grass, foxtail and velvetleaf
For each pot (2–20 plants/pot), a rating of 1–5 given, where 5 was complete desiccation of all plants
All treatments included 1.125% Emsorb 6900 (v/v)

Example 29

Synergistic relationships with caprylic/capric acids (c/c)

| Average relative injury rating* | | Average rating | Treatment Ingredients |
|---|---|---|---|
| 60 G/acre | Spray to drip | per pot | Compound (1%) |
| 4.5  | 4.57 | 4.52 |  | 3% c/c |
| 4.49 | 4.59 | 4.54 | urea | 3% c/c |
| 4.56 | 4.33 | 4.45 | sorbic acid | 3% c/c |
| 4.46 | 4.33 | 4.4  | di-sodium succinate | 3% c/c |
| 4.62 | 4.5  | 4.58 | ammonium tartrate | 3% c/c |
| 4.53 | 4.52 | 4.53 | methyl salicylate | 3% c/c |
| 4.56 | 4.47 | 4.52 | potassium salicylate | 3% c/c |
| 4.6  | 4.61 | 4.61 | succinic acid | 3% c/c |

*For 60 G/a: 10 total pots/treatment, testing lambsquarter, pigweed, foxtail and barnyard grass
*For spray to drip: 5 total pots/treatment, testing pigweed, sudan grass, foxtail, barnyard grass and velvetleaf
For each pot (2–20 plants/pot), a rating of 1 to 5 given, where 5 was complete injury/desiccation of all plants -continued Synergistic relationships with caprylic/capric acids (c/c)

| Average relative injury rating* | | Average rating | Treatment Ingredients |
|---|---|---|---|
| 60 G/acre | Spray to drip | per pot | Compound (1%) | c/c = Caprylic, capric, caproic and lauric at 58, 40, 1 and 1%, respectively; i.e., Henkel's Emery 658, used at v/v, in water

Example 30

Herbicidal activity on cotton foliage: synergistic relationships between succinic acid and caprylic/capric acid (c/c) combinations

| | | Total injury ratings, combined, for two separate evaluations* | |
|---|---|---|---|
| Treatment | | 60 G/a | Average rating/pot |
| 1 | 4% c/c | 18.5 | 3.08 |
| 2 | 4% c/c + 0.5% succinic acid | 21.4 | 3.57 |
| 3 | 5% c/c | 22.4 | 3.73 |
| 4 | 5% c/c + 0.5% succinic acid | 25.7 | 4.28 |
| 5 | 6% c/c | 25.3 | 4.22 |

*For 60 G/a: 3 total pots/treatment, testing cotton (DeltaPine NuCotn 33b)
For each pot, a rating of 1–5 was given, where 5 was complete desiccation of all foliage
Two independent evaluations (ratings) completed
All treatments included Emsorb 6900 (Henkel) at 1%
Caprylic/capric (caprylic, capric, caproic and lauric at 58, 40, 1 and 1%, respectively), Henkel's Emery 658, used at v/v, in water
Since succinic acid tested alone had a rating of zero, caprylic/capric + succinic acid was synergistic
Herbicidal activity: 5% c/c + 0.5% succinic acid > 6% c/c

Example 31

Herbicidal activities: synergistic relationships between succinic acid and caprylic/capric acid (c/c) combinations

| Treatment | | Total injury ratings, combined for two separate evaluation* | | | Average rating per pot |
|---|---|---|---|---|---|
| | | 60 G/a | Spray to drip | Total Rating | |
| 1 | 4% c/c | 123.3 | 41.5 | 164.8 | 4.12 |
| 2 | 4% c/c + 0.5% succinic acid | 128.1 | 45.1 | 173.2 | 4.33 |
| 3 | 5% c/c | 129.9 | 46.3 | 176.2 | 4.41 |
| 4 | 5% c/c + 0.5% succinic acid | 134.5 | 46.5 | 181   | 4.53 |
| 5 | 6% c/c | 133.9 | 46.8 | 180.7 | 4.52 |

*For 60 G/a: 10 total pots/treatment, testing nightshade, pigweed, foxtail barnyard grass, sudan grass and cotton (DeltaPine NuCotn 33b)
*For spray to drip: 5 total pots/treatment, testing Kentucky bluegrass, nutsedge, barnyard grass, sudan grass and foxtail
For each pot (2–20 plants/pot), a rating of 1 to 5 given, where 5 was complete desiccation of all plants
Two independent evaluations (ratings) done for plants treated at both 60 G/a and spray to drip
All treatments included Emsorb 6900 (Henkel) at 1%
Caprylic/capric (caprylic, capric, caproic and lauric at 58, 40, 1 and 1%, respectively), Henkel's Emery 658, used at v/v, in water
Since succinic acid, alone had a rating of zero, caprylic/capric + succinic acid was synergistic

Example 32

General screening of candidate compounds: to examine for synergistic relationships with caprylic/capric acids (c/c)

| Average relative injury rating* | | | Spray to drip | Average rating per pot | Treatment Ingredients Compound (equimolar amounts) | c/c |
|---|---|---|---|---|---|---|
| 40 G/ acre | 60 G/ acre | | | | | |
| 4.21 | 4.43 | 4.44 | 4.35 | | | 3% c/c |
| 4.35 | 4.47 | 4.54 | 4.44 | succinic acid (1%) + | | 3% c/c |
| 4.35 | 4.49 | 4.61 | 4.47 | ammonium succinate (1.26%) + | | 3% c/c |
| 4.36 | 4.42 | 4.4 | 4.4 | ammonium sulfate (1.12%) + | | 3% c/c |
| 4.35 | 4.5 | 4.59 | 4.47 | ammonium tartrate (1.42%) + | | 3% c/c |

*For 40 G/a: 10 total pots/treatment, testing chickweed, lambsquarter, Kentucky bluegrass, redtop and rye
*For 60 G/a: 10 total pots/treatment, testing giant and green foxtail, pigweed and crabgrass
*For spray to drip: 7 total pots/treatment, testing Kentucky bluegrass, nutsedge, pigweed, Johnson grass, foxtail and sudan grass
For each pot (2–20 plants/pot), a rating of 1 to 5 given, where 5 was complete injury/desiccation of all plants
c/c = Caprylic, capric, caproic and lauric at 58, 40, 1 and 1%, respectively; i.e., Henkel's Emery 658, used at v/v, in water

Example 33

Herbicidal activity storage stability of fatty acid/succinic acid-based formulations
Formulations stored one week (average day and night time temperatures were 90 and 75 degrees, Fahrenheit, in the greenhouse) and re-tested, via spray to drip applications on same test plant varieties
4% caprylic, 4% caprylic/capric and 4% pelargonic (+/- 0.5% succinic acid) were tested or a total of 6 formulations, each containing 1.125% Emsorb 6900 (Henkel)

| | Average scores, for all 6 formulations (rating per pot, 2–20 plants/pot) | |
|---|---|---|
| | Before storage | After storage |
| Barnyard grass | 4.73 | 4.8 |
| Foxtail | 4.68 | 4.68 |

A rating of 1–5 was given, where 5 was complete desiccation of all plants
Fatty acids were v/v and succinic acid was wt/v, in water
Note: ratings for individual fatty acid treatments (+/- succinic acid), before and after storage, were similar

Example 34

Herbicidal combinations of caprylic/capric (c/c) or pelargonic acid, with equimolar amounts of succinic acid and ammonium succinate, on weed varieties

| Treatment | Total Injury ratings* | | | | Average rating/pot |
|---|---|---|---|---|---|
| | 40 G/a | 60 G/a | Spray to drip | Total | |
| 1  3% c/c | 85.5 | 60.2 | 36.1 | 181.8 | 4.33 |
| 2  3% c/c + 1% succinic acid | 88.1 | 62.5 | 36.7 | 187.3 | 4.46 |
| 3  3% c/c + 1.26% ammonium succinate | 88.8 | 60.8 | 37.4 | 187 | 4.45 |
| 4  3% pelargonic acid | 87.7 | 60.8 | 37.3 | 185.8 | 4.42 |
| 5  3% pelargonic acid + 1% succinic acid | 865.9 | 62.2 | 38 | 187.1 | 4.45 |
| 6  3% pelargonic acid + 1.26% ammonium succinate | 87.6 | 61.2 | 36.9 | 185.7 | 4.42 |

*For 40 G/a: 10 total pots/treatment, testing crab grass, chickweed and common lambsquarter
*For 60 G/a: 7 total pots/treatment, testing redtop, pigweed, foxtail
For spray to drip: 8 total pots/treatment, testing barnyard grass, foxtail, sudan grass and nutsedge
For each pot (2–20 plants/pot), a rating of 1 to 5 given, where 5 was complete desiccation of all plants
Two independent evaluations for both 40 and 60 G/a and one evaluation for spray to drip
All treatments included Emsorb 6900 (Henkel) at 1%
Caprylic/capric (caprylic, capric, caproic and lauric at 58, 40, 1 and 1% respectively), i.e., Henkel's Emery 658, used at v/v, in water
Amounts of succinic acid and ammonium succinate used were equimolar amounts
Since succinic acid (or ammonium succinate) tested alone had a rating of zero, pelargonic acid (or c/c) + succinic acid (or ammonium succinate) were synergistic. The exception was: 3% pelargonic acid + 1.26% ammonium succinate

Example 35

Enhancement of RoundUp Ultra (+/- ammonium sulfate or Ams) herbicidal activity, using succinic acid amendments
RoundUp Ultra at 1 pint/acre (No Sylgard or any other surfactant used)

| | | Days after treatment: relative injury ratings | | | | Average rating per pot |
|---|---|---|---|---|---|---|
| | | Day #6 | Day #9 | Day #11 | Day #14 | |
| 1 | RU | 10.5 | 17.1 | 15.9 | 17.5 | 1.91 |
| 2 | RU + ams | 18.3 | 17.6 | 18.4 | 21.6 | 2.37 |
| 3 | RU + ams + 0.5% succinic acid | 21 | 20.3 | 24.3 | 25.7 | 2.85 |
| 4 | RU + ams + 1.5% succinic acid | 19.4 | 18.6 | 24.2 | 27.3 | 2.8 |
| 5 | RU + 0.5% succinic acid | 16.7 | 14.2 | 16 | 20.5 | 2.11 |
| 6 | RU + 1.5% succinic acid | 16.8 | 16.1 | 18.6 | 23.6 | 2.35 |

*8 total pots/treatment, testing Kentucky bluegrass, barnyard grass, crab grass, pigweed, redtop, nutsedge, wheat and foxtail.
For each pot (2–20 plants/pot), a rating of 1 to 5 given, where 5 was complete injury/desiccation of all plants
RoundUp Ultra was at 1 pint/acre and ammonium sulfate, when used, was at 2%
Spray application at 60 G/acre
Succinic acid tested alone had a rating of zero. RoundUp Ultra, alone or RoundUp Ultra + ammonia sulfate were synergistic with succinic acid

Example 36

Enhancement of RoundUp Ultra (+/− ammonium sulfate or Ams) herbicidal activity, using succinic acid amendments RoundUp Ultra at 1 pint/acre

| | | Days after treatment: relative injury ratings | | | Average |
|---|---|---|---|---|---|
| | Treatment | Day #6 | Day #9 | Day #11 | Day #14 | rating per pot |
| 1 | RU | 29 | 30.2 | 31.5 | 29.8 | 3.35 |
| 2 | RU + ams | 30.8 | 32.9 | 34.7 | 32.5 | 3.64 |
| 3 | RU + ams + 0.5% succinic acid | 30.2 | 32.7 | 35.5 | 34.5 | 3.69 |
| 4 | RU + ams + 1.5% succinic acid | 34.6 | 35.7 | 37.8 | 37.4 | 4.04 |
| 5 | RU + 0.5% succinic acid | 32.8 | 33.9 | 35.1 | 35.4 | 3.81 |
| 6 | RU + 1.5% succinic acid | 32.5 | 31.2 | 32.6 | 32.5 | 3.58 |

*9 total pots/treatment, testing barnyard grass, green foxtail, sudan grass and pigweed.
For each pot (2–20 plants/pot), a rating of 1 to 5 given, where 5 was complete injury/desiccation of all plants
RoundUp Ultra was at 1 pint/acre and ammonium sulfate, when used, was at 2%
Sylgard 309 (0.3%) added immediately before spray application at 60 gallons/acre
Succinic acid tested alone had a rating of zero. RoundUp Ultra, alone or RoundUp Ultra + ammonium sulfate were synergistic with succinic acid.

Example 37

Enhancement of RoundUp Ultra (+/− ammonium sulfate or Ams) herbicidal activity, using succinic acid amendments RoundUp Ultra (RU) at 1 quart per acre

| | | Days after treatment: relative injury ratings* | | | | | Average |
|---|---|---|---|---|---|---|---|
| | Treatment | Day #5 | Day #8 | Day #10 | Day #13 | Day 17 | rating per pot |
| 1 | RU | 32.7 | 29.9 | 28.6 | 29.5 | 31.4 | 3.8 |
| 2 | RU + ams | 33.3 | 33.6 | 30.7 | 34.5 | 36.6 | 4.22 |
| 3 | RU + ams + 0.5% succinic acid | 34 | 34.5 | 32.4 | 35.3 | 36.7 | 4.32 |
| 4 | RU + ams + 1.5% succinic acid | 35.3 | 35.6 | 32.5 | 35.3 | 38.4 | 4.43 |
| 5 | RU + 0.5% succinic acid | 33.8 | 30.9 | 30.3 | 31 | 33.1 | 3.98 |
| 6 | RU + 1.5% succinic acid | 33.7 | 30.2 | 31 | 33.6 | 34 | 4.06 |

*8 total pots/treatment, testing sudan grass, green foxtail, barnyard grass and pigweed
For each pot (2–20 plants/pot), a rating of 1 to 5 given, where 5 was complete injury/desiccation of all plants
RoundUp Ultra was at 1 quart/acre and ammonium sulfate, when used, was at 2%, wt/v
Sylgard 309 (0.3%) added immediately before spray application at 60 gallons/acre
Succinic acid tested alone had a rating of zero. RoundUp Ultra, alone or RoundUp Ultra + ammonium sulfate were synergistic with succinic acid

Example 38

Enhancement of herbicidal activity of RoundUp Ultra/ammonium sulfate testing selected amendments

| | Treatment | pH, spray solution | Days after treatment: injury ratings* | | | | average | per test |
|---|---|---|---|---|---|---|---|---|
| | | | day #4 | day #7 | day 11 | day #13 | average | |
| 1 | RU/ams | 4.51 | 32.3 | 44.1 | 50 | 50.8 | 44.3 | 4.03 |
| 2 | RU/ams + succinic acid | 1.77 | 39.3 | 46.3 | 50.7 | 51.4 | 46.9 | 4.26 |
| 3 | RU + ams + ammonium succinate | 3.71 | 36.2 | 46.2 | 51.3 | 52.3 | 46.5 | 4.23 |
| 4 | RU + ams ammonium tartrate | 4.78 | 35.7 | 46 | 49.3 | 50.2 | 45.3 | 4.12 |
| 5 | RU/ams + tartaric acid | 1.27 | 33.9 | 46.9 | 50.7 | 51.5 | 46.2 | 4.2 |
| 6 | RU/ams + citric acid | 1.38 | 34.6 | 46.7 | 50.7 | 51.4 | 45.7 | 4.15 |
| 7 | RU/ams + L-malic acid | 1.59 | 34.6 | 47.7 | 51.1 | 51.8 | 46.3 | 4.21 |
| 8 | RU/ams + acetic acid | 2.51 | 33.7 | 47.1 | 50.8 | 51.3 | 45.7 | 4.15 |

*11 total pots/treatment, testing velvetleaf, crab grass, sudan grass, redtop, green foxtail and barnyard grass.
For each pot (2–20 plants/pot), a rating of 1 to 5 given, where 5 was complete desiccation
Equimolar amounts of amendments used: 1.5% succinic acid, 1.89% ammonium succinate, 2.17% ammonium tartrate, 1.91% tartaric acid, 2.45% citric acid, 1.71% L-malic acid, 0.77% acetic acid
RoundUp Ultra (1.5 pints/acre) and 2% ammonium sulfate (ams) used in all treatments
Sylgard (0.3%) added immediately before spray application at 60 gallons/acre
Amendments used independently had a rating of zero. All amendments had a synergistic relationship with RU/ams; i.e., each amendment enhanced RU/ams herbicidal activity over ratings for RU/ams (containing no amendments).
No apparent correlation between pH of spray solutions (including Sylgard) and herbicidal activity was found.

Example 39

Enhancement of herbicidal activity of caprylic/capric acids (c/c), using selected compounds at equimolar amounts

| Treatmeat | Days after treatment: relative injury ratings* | | | Average rating per pot |
|---|---|---|---|---|
| | Day #2 | Day #4 | Day #5 | |
| 1  3% c/c | 30 | 27.6 | 30.3 | 3.66 |
| 2  3% c/c + succinic acid (1%) | 35.8 | 33.6 | 35.1 | 4.35 |
| 3  3% c/c + di-ammonium succinate (1.26%) | 35.1 | 32.5 | 34.2 | 4.24 |
| 4  3% c/c + ammonium sulfate (1.12%) | 35.5 | 33.6 | 34.4 | 4.3 |
| 5  3% c/c + ammonium tartrate (1.42%) | 35.9 | 33.6 | 34.2 | 4.32 |
| 6  succinic acid (1%) | 0 | 0 | 0 | 0 |
| 7  di-ammonium succinate (1.26%) | 0 | 0 | 0 | 0 |
| 8  ammonium sulfate (1.12%) | 0 | 0 | 0 | 0 |
| 9  ammonium tartrate (1.42%) | 0 | 0 | 0 | 0 |

*8 total pots/treatment, testing chickweed, redtop, velvetleaf, crabgrass and green foxtail
For each pot (2–20 plants/pot), a rating of 1 to 5 given, where 5 was complete injury/desiccation of all plants
All treatments included 0.86% Emsorb 6900 and 0.43% mineral oil
c/c = Caprylic, capric, caproic and lauric at 58, 40, 1 and 1% respectively; i.e., Henkel's Emery 658, used at v/v, in water
Application volume was 40 G/acre
Synergistic relationships exist between 3% c/c and each amendment test tested

Example 40

Desiccation of cotton foliage: Interaction of RoundUp Ultra and caprylic acid/capric acid (+/− succinic acid)

| Treatmeat | | Day after treatment: average ratings | | | | | | Total Rating |
|---|---|---|---|---|---|---|---|---|
| | | 1 | 2 | 5 | 7 | 10 | 12 | |
| 1  RU + 2% AMS | | 0 | 0 | 6 | 6 | 7 | 7 | 26 |
| 2  RU + 2% AMS | 4% c/c | 18 | 16 | 15 | 15 | 15 | 16 | 95.9 |
| 3  RU + 2% AMS | 4% c/c + 1% succinic acid | 18 | 17 | 17 | 17 | 16 | 18 | 103.2 |
| 4  RU + 2% AMS | 1% succinic acid | 0 | 0 | 7.2 | 6.5 | 7.7 | 8.8 | 30.2 |
| 5  2% AMS | 4% c/c + 1% succinic acid | 18 | 17 | 18 | 17 | 18 | 17 | 105.4 |
| 6  2% AMS | 4% c/c | 18 | 17 | 18 | 18 | 18 | 17 | 104.8 |

*Visual rating of 1 to 5, where 5 = complete desiccation of all cotton plants (4 plants per treatment group, each plant receiving a rating of 1–5)
Cotton variety = DeltaPine NuCotn 33b, at open boll, when treated
RoundUp Ultra at 1 quart/acre delivered at 60 G/a
Each treatment contained 1.14% Emsorb 6900 and 0.57% mineral oil
Caprylic/capric (caprylic, capric, caproic and lauric at 58, 40,1 and 1% respectively), i.e., Henkels, Emery 658, used at v/v, in water
AMS = ammonium sulfate
Succinic acid had a rating of zero.
Combination of succinic acid with other ingredients was synergistic.

Example 41

Synergistic relationship between succinic acid and caprylic/capric acids C/C, relating to herbicidal activity

| | | | Injury ratings based on 2 independent evaluations* | | |
|---|---|---|---|---|---|
| | Treatment | 40 G/a | 60 G/a | Total | Average rating per pot |
| 1 | 4% caprylic/capric | 87.3 | 80.7 | 168 | 4.42 |
| 2 | 4% caprylic/capric + 1% succinic | 88.6 | 82.1 | 170.7 | 4.49 |
| 3 | 4% caprylic/capric + 0.5% succinic | 89.9 | 82.7 | 172.6 | 4.54 |
| 4 | 4% caprylic/capric + 0.5% succinic + 0.5% sodium salicylate | 90.3 | 82.6 | 172.9 | 4.55 |
| 5 | 0.5% succinic acid | 0 | 0 | 0 | 0 |
| 6 | 0.5% sodium salicylate | 1 | 0.5 | 1.5 | 0.04 |
| 7 | 5% caprylic/capric | 92 | 82.8 | 174.8 | 4.6 |
| 8 | 5% caprylic/capric + 0.5% succinic acid | 91.6 | 83.9 | 175.5 | 4.62 |

*For each pot, a rating (1 to 5) was given, where 5 was complete desiccation of all plants
Two independent evaluations were made for both 40 and 60 gallons/acre applications
For 40 G/acre: Canadian thistle, velvet leaf, Johnson grass and giant foxtail
For 60 G/acre: velvetleaf, Johnson grass and giant foxtail were tested
C/C = Caprylic, capric, caproic and lauric at 58, 40, 1 and 1%, respectively; i.e., Henkel's Emery 658, used at v/v, in water
Succinic acid and sodium salicylate were added at wt/volume
All treatments included Henkel's Emery 6900 and mineral oil; i.e., for each 1% of caprylic/capric, 0.286 and 0.143% of 6900 and mineral oil were included in each treatment

Example 42

Herbicidal activity: comparison of caprylic, pelargonic and an equimolar mixture of caprylic and pelargonic acids

| | | | Injury ratings based on 2 independent evaluations* | |
|---|---|---|---|---|
| | Treatments (equimolar comparison) | 40 G/acre | 60 G/acre | Average rating per pot |
| 1 | 3% caprylic | 40.8 | 51.6 | 4.16 |
| 2 | 3.375% pelargonic | 43 | 53.6 | 4.41 |
| 3 | 1.5% caprylic + 1.69% pelargonic | 43 | 53.6 | 4.41 |
| 4 | 4% caprylic | 44.1 | 54.5 | 4.49 |
| 5 | 4.5% pelargonic | 45.1 | 53.9 | 4.51 |
| 6 | 2% caprylic + 2.25% pelargonic | 44.6 | 54.2 | 4.51 |

*For each pot, a rating (1 to 5) was given, where 5 was complete desiccation of all plants
For 40 G/acre: chickweed, redroot pigweed, lambsquarter and green foxtall were tested
For 60 G/acre: chickweed, redroot pigweed, lambsquarter, green foxtall, crabgrass and wheat were tested
Caprylic and pelargonic acids were used at volume/volume
All treatments included Henkel's Emsorb 6900 and mineral oil: for each 1% of caprylic or pelargonic acid, 0.286 and 0.143% of 6900 and mineral oil were included in each treatment.

Example 43

Herbicidal enhancement of pelargonic by succinic acid and diammonium succinate

| | | | Injury ratings based on 2 independent evaluations* | | |
|---|---|---|---|---|---|
| | Treatment | 40 G/a | 60 G/a | Spray to drip | Average rating per pot |
| 1 | 2.5% Scythe active ingredients | 78.7 | 103 | 53.6 | 4.36 |
| 2 | 2.5% pelargonic | 79.2 | 102.2 | 53.8 | 4.36 |
| 3 | 2.5% pelargonic + 0.5% succinic | 81.7 | 105.1 | 55.3 | 4.48 |
| 4 | 2.5% pelargonic + 2% succinic | 80.2 | 105.5 | 55.1 | 4.46 |
| 5 | 2.5% pelargonic + 2% diammonium succinate | 80.9 | 105.4 | 54.4 | 4.46 |
| 6 | 2.22% caprylic/capric (C/C) | 80.3 | 103.4 | 51.5 | 4.36 |

*For each pot, a rating (1 to 5) was given, where 5 was complete desiccation of all plants
40 G/a: lambsquarter, velvetleaf and green foxtail were tested
60 G/a: pigweed, chickweed, crabgrass, green foxtail, velvetleaf, lambsquarter and wheat were tested
Spray to drip: nutsedge, velvetleaf, green foxtail, giant foxtail and barnyard grass were tested
c/c = Caprylic, capric, caproic and lauric at 58, 40, 1 and 1%, respectively, i.e., Henkel's Emery 658, used at v/v, in water
The active ingredients in Scythe, (pelargonic acid) and caprylic/capric (Henkel's Emery 658) were compared on equimolar basis

Example 44

Synergistic Relationship between Succinic or Citric acid and Caprylic Acid, Testing Dry Beans Treatment effects 3 days after single, foliar application

| | Green Foliage | | Yellow Foliage | |
|---|---|---|---|---|
| Treatment | Overall Effect | Foliage Affected (%) | Overall Effect | Foliage Affected (%) |
| Na Salicylate (2%) | 5 | 90 | 5 | >90 |
| Na Salicylate (0.5%) | 2 | 5–10 | 1 | 30 |
| Na Salicylate (0.5%) + Citric Acid (0.5%) | 1 | 5–10 | 1 | 30 |
| Na Salicylate (0.5%) + Succinic Acid (0.5%) | 1.5 | 5–10 | 1 | >40 |
| Citric Acid (0.5%) | 0 | 0 | 0 | 0 |
| Succinic Acid (0.5%) | 0 | 0 | 0 | 0 |
| Caprylic Acid (0.5%) | 2.5 | 10–15 | 2 | 70 |
| Caprylic Acid (0.5%) + Citric Acid (0.5%) | 3.5 | 30 | 3 | 90 |
| Caprylic Acid (0.5%) + Succinic Acid (0.5%) | 4 | 50 | 4 | >90 |

Overall effect: higher scores = greater effect (where 5 equals profound desiccation)
Dry bean variety = Vista
Citric acid and succinic acid showed synergistic effect

Example 45

Greater Effect by Succinic Acid over-Calcium Succinate, when used with Sodium Salicylate, Testing Several Plant Varieties*

| Treatments | overall effect, 9 evaluations (average) |
|---|---|
| Sodium Salicylate (1%) + Succinic Acid (1%) | 2.89 |
| Sodium Salicylate (1%) + Calcium Succinate (1%) | 1.44 |

Overall effect: higher score = greater effect (where 5 equals profound desiccation)
*Test plants: weed varieties, shrub foliage, covergrass, turf and soybeans

Example 46

Confirmation of Example 45, Testing Turf and Shrub Foliage Treatment effects 1, 2, 4 and 7 days after a single, foliar application

| Treatments | Overall effect, 17 evaluations (average) |
|---|---|
| Sodium Salicylate (1%) | 1.35 |
| Sodium Salicylate (1%) + Succinic Acid (2%) | 2.59 |
| Sodium Salicylate (1%) + Calcium Succinate (2%) | 2.18 |
| Succinic Acid (2%) | 0.24 |

Overall effect: higher score = greater effect (where 5 equals profound desiccation)
Succinic acid and calcium succinate showed synergistic effect

Example 47

Effects of desiccants and desiccant combinations with other compounds on young potato plants

| | Treatment | Injury ratings of treated plants (hours or days after application) | | | | | | | All evaluations |
|---|---|---|---|---|---|---|---|---|---|
| # | ingredients | 1.5 hr | 1 | 3 | 6 | 17 | 22 | 27 | (total score) |
| 1 | 1% caprylic | 2 | 2 | 3 | 2 | 2.5 | 3 | 3 | 17.5 |
| 2 | 1% caprylic + 0.5% tartaric + 0.5% NaSal | 3 | 5 | 5.5 | 5 | 5.5 | 5.5 | 4 | 29.5 |
| 3 | 1% caprylic + 1% tartaric | 2 | 3 | 3.5 | 3 | 3.4 | 4 | 3 | 23 |
| 4 | 1% caprylic + 0.5% dimethyl succinic acid | 2 | 3 | 3 | 3 | 3 | 3.5 | 3 | 21.5 |
| 5 | 1% caprylic + 0.5% beta-alanine | 1 | 2 | 2 | 2 | 2.5 | 3 | 2.5 | 15 |
| 6 | 1% caprylic + 1% succinic | 3 | 4 | 3 | 4 | 5 | 5.5 | 4.5 | 30 |
| 7 | 2% caprylic | 3.5 | 5 | 5 | 5 | 5 | 5.5 | 5.5 | 34.5 |

Effects of desiccants and desiccant combinations with other compounds on young potato plants

| | Treatment | Injury ratings of treated plants (hours or days after application) | | | | | | | All evaluations |
|---|---|---|---|---|---|---|---|---|---|
| # | ingredients | 1.5 hr | 1 | 3 | 6 | 17 | 22 | 27 | (total score) |
| 8 | 2% caprylic + 0.5% tartaric + 0.5% NaSal sodium salicylate | 4.5 | 6 | 6 | 6 | 6 | 6 | 6 | 40.5 |
| 9 | 2% caprylic + 1% tartaric | 3.5 | 5 | 5 | 5 | 5 | 5.5 | 5.5 | 34.5 |

Caprylic acid and dimethyl succinic acid added v/v; all other compounds added at wt/v.

All solutions in 50% acetone, with solution (20 mls) sprayed 2 feet from plant canopy. Helena Kinetic at 0.2% included in each solution. All plants grown in green house (day time temp 80–100 degrees, Fahrenheit)

Higher evaluation scores represent greater degree of vine and foliage desiccation. A "6" = complete desiccation.

Summary: a) addition of succinic or tartaric acid to 1% caprylic acid >> 1% caprylic acid, (b) combination of NaSal + tartaric (or succinic acid) to caprylic acid were the best treatments

Example 48

Synergistic Relationships Between:
Succinic Acid + Caprylic Acid
Succinic Acid + Sodium Salicylate
Treatment effects 3 days after a single, foliar application, testing soybeans

| Treatment | Overall Effect | Foliage Affected (%) |
|---|---|---|
| Caprylic Acid (1%) | 2.5 | 25–30 |
| Caprylic Acid (1%) + Succinic Acid (1%) | 3 | 30–35 |
| Succinic Acid (1%) | 0 | 0 |
| Sodium Salicylate (1%) | 1.5 | 5–20 |
| Sodium Salicylate (1%) + Succinic Acid (1%) | 3.5 | 40–50 |

Overall effect: higher scores = greater effect (where 5 equals profound desiccation)
Soybean variety = Stine 2250

Example 49

Enhancement of Scythe's herbicidal activity by selected compounds

| | | Independent evaluations of snapbean and potato plants, hours/days after application of desiccants | | | | | | | Totals, all evaluations | | |
|---|---|---|---|---|---|---|---|---|---|---|---|
| | | 1.5 hours | | 2 days | | 11 days | | 15 days | | | Pota- | |
| Treatment # | Treatment Ingredients | beans | potatoes | beans | potatoes | beans | potatoes | beans | potatoes | Beans | toes | All |
| 1 | 2% Na Salicylate | 1 | 0 | 1 | 1 | 1.5 | 1 | 1 | 1 | 4.5 | 3 | 7.5 |
| 2 | 4% Scythe | 3 | 3 | 3.5 | 2.5 | 2 | 2 | 1 | 2 | 9.5 | 9.5 | 19 |
| 3 | 4% Scythe + 2% NaSal | 4 | 3 | 5 | 3.5 | 3 | 3 | 2 | 3 | 14 | 12.5 | 26.5 |
| 4 | 4% Scythe + 0.25% tartaric | 4 | 3 | 4 | 3 | 2.5 | 2.5 | 3 | 2 | 13.5 | 10.5 | 24 |
| 5 | 4% Scythe + 0.5% tartaric | 4 | 4 | 5.5 | 3 | 3 | 2 | 4 | 15 | 16.5 | 10.5 | 27 |
| 6 | 4% Scythe + 1% tartaric | 4 | 3.5 | 6 | 3.5 | 3 | 3 | 3 | 2 | 16 | 12 | 28 |
| 7 | 4% Scythe + 1% NaSal | 3 | 3 | 4.5 | 3 | 2.5 | 2.5 | 2 | 2 | 12 | 10 | 22 |
| 8 | 4% Scythe + 0.5% NaSal | 3 | 3 | 4.5 | 2 | 1.5 | 1.5 | 1 | 1.5 | 10 | 8 | 18 |
| 9 | 4% Scythe + 1% caprylic | 4 | 4.5 | 5 | 3.5 | 2 | 3.5 | 1 | 3.5 | 12 | 15 | 27 |
| 10 | 4% Scythe + 0.5% tartaric + 0.5% NaSal | 4 | 5 | 5.5 | 5 | 3.5 | 4 | 3 | 5 | 16 | 19 | 35 |
| 11 | 4% Scythe + 1% citric acid | 4 | 3 | 6 | 3 | 2.5 | 2 | 2 | 2 | 145 | 10 | 24.5 |

Solutions applied at 40 gallons/acre, containing 0.1% Helena Kinetic. All plants grown in greenhouse (day temperature was 80–100 degrees, fahrenheit). Higher rating scores represent greater degree of desiccation. A "6" = complete desiccation. Scythe and caprylic acid added v/v. All other compounds added wt/v.
Summary: a) all combinations with Scythe (except 0.5% NaSal) improved performance, b) best combination was 4% Scythe with 0.5% tartaric + 0.5% NaSal, c) increasing the concentratio of tartaric acid with 4% Scythe had little effect

Example 50

Synergistic Relationships-Between Succinic Acid and Caprylic Acid at Different Application Rates, Testing Soybeans
Treatment effects 2 days after a single, foliar application

| | Two Independent Sites (average of 2 sites) | |
|---|---|---|
| | Overall Effect | Foliage Affected (%) |
| Caprylic Acid (0.2%) | 0.5 | 1.25 |
| Caprylic Acid (0.5%) | 2.25 | 9 |
| Caprylic Acid (1.0%) | 4 | 22.3 |
| Caprylic Acid (0.2%) + Succinic Acid (1.0%) | 1.5 | 6.5 |
| Caprylic Acid (0.5%) + Succinic Acid (1.0%) | 3 | 15 |
| Caprylic Acid (1.0%) + Succinic Acid (1.0%) | 4.25 | 26 |
| Succinic Acid (1.0%) | 0 | 0 |
| Caprylic Acid (0.5%) + L-Lactic Acid (1.0%) | 2.75 | 15 |
| L-Lactic Acid (1.0%) | 0.5 | 1.25 |

Overall effect: higher scores = greater effect (where 5 equals profound desiccation)
Soybean variety Stine 2250
Succinic acid and lactic acid had synergistic effect

Example 51

Synergy Comparisons of Various Organic Acids with Caprylic Acid, Testing Soybeans
Treatment effects 3 days after a single, foliar application

| | Two Independent Sites (average of 2 sites) | |
|---|---|---|
| | Overall Effect | Foliage Affected (%) |
| Caprylic Acid (0.5%) | 1.5 | 5 |
| Caprylic Acid (0.5%) + L-Tartaric Acid (0.5%) | 2.75 | 17.5 |
| Caprylic Acid (0.5%) + L-Malic Acid (0.5%) | 2 | 11.5 |
| Caprylic Acid (0.5%) + Succinic Acid (0.5%) | 2.25 | 12.5 |
| Caprylic Acid (0.5%) + L-Lactic Acid (0.5%) | 2.25 | 11.5 |
| Caprylic Acid (0.5%) + Citric Acid (0.5%) | 2.75 | 17.5 |
| L-Tartaric Acid (0.5%) | 0 | 0 |
| L-Malic Acid (0.5%) | 0 | 0 |
| Succinic Acid (0.5%) | 0 | 0 |
| L-Lactic Acid (0.5%) | 0 | 0 |
| Citric Acid (0.5%) | 0 | 0 |

Overall effect: higher scores = greater effect (where 5 equals profound desiccation)
Soybean variety = Stine 2250
Tartaric, malic, succinic, lactic and citric acid showed synergistic effects

Example 52

Synergistic Relationships Between Succinic Acid and Caprylic Acid (or Sodium Salicylate), Testing Turf
Treatment effects 2 days after a single, foliar application

| Treatments | Overall Effect |
|---|---|
| Caprylic Acid (1.0%) | 2 |
| Caprylic Acid (1.0%) + Succinic Acid (0.5%) | 3 |
| Succinic Acid (0.5) | 0 |
| Sodium Salicylate (1.0%) | 1.5 |
| Sodium Salicylate (1.0%) + Succinic Acid (0.5%) | 2 |

Overall effect: higher scores = greater effect (where 5 equals profound desiccation)

Example 53

Effects of Various Compounds on Caprylic Acid Testing Turf and Covergrass Treatment effects 1, 3, 6, 7 and 11 days after a single, foliar application at two, independent sites

| Treatments | Overall Effect 10 Evaluations (average) |
|---|---|
| Caprylic Acid (1.0%) | 2.45 |
| Caprylic Acid (1.0%) + Adipic Acid (0.5%) | 2.6 |
| Caprylic Acid (1.0) + L-Tartaric Acid (0.5%) | 3.8 |
| Caprylic Acid (1.0%) + Unipine (0.5%) | 3.45 |
| Caprylic Acid (1.0%) + Sodium Salicylate (0.5%) | 3.1 |

Overall effect: higher scores = greater effect (where 5 equals profound desiccation)
Adipic acid, tartaric acid, unipine and sodium salicylate showed synergistic effects

Example 54

Effects of Various Compounds on Caprylic Acid Testing Turf and Shrub Foliage Treatment effects 3, 4, 6 and 7 days after a single, foliar application

| Treatments | Overall Effect 29 Evaluations (average) |
|---|---|
| Caprylic Acid (1.0%) | 1.05 |
| Caprylic Acid (1.0%) + Adipic Acid (0.5%) | 2.19 |
| Caprylic Acid (1.0) + L-Malic Acid (0.5%) | 1.4 |
| Caprylic Acid (1.0%) + L-Tartaric Acid (0.5%) | 2.19 |
| Caprylic Acid (1.0%) + Unipine (0.5%) | 2.4 |
| Caprylic Acid (1.0%) + Sodium Salicylate (0.5%) | 2.05 |
| Caprylic Acid (1.0%) + Succinic Acid (0.5%) | 1.95 |
| Caprylic Acid (1.0%) + L-Lactic Acid (0.5%) | 2.16 |
| Caprylic Acid (1.0%) + Citric Acid (0.5%) | 1.47 |

Overall effect: higher scores = greater effect (where 5 equals profound desiccation)
Adipic acid, tartaric acid, unipine, sodium salicylate, succinic acid, lactic acid and citric acid showed synergistic effects

Example 55

Measurement of pH Values for Test Desiccants

| | pH Value |
|---|---|
| Caprylic Acid (0.5%) | 3.30 |
| Caprylic Acid (0.5%) + L-Tartaric Acid (0.5%) | 1.07 |
| Caprylic Acid (0.5%) + L-Malic Acid (0.5%) | 1.49 |
| Caprylic Acid (0.5%) + Succinic Acid (0.5%) | 1.67 |
| Caprylic Acid (0.5%) + L-Lactic Acid (0.5%) | 1.69 |
| Caprylic Acid (0.5%) + Citric Acid (0.5%) | 1.51 |
| L-Tartaric Acid (0.5%) | 1.52 |
| L-Malic Acid (0.5%) | 1.69 |
| Succinic Acid (0.5%) | 1.94 |
| L-Lactic Acid (0.5%) | 1.93 |
| Citric Acid (0.5%) | 1.64 |
| Caprylic Acid (0.5%) | 3.55 |
| Caprylic Acid (0.5%) + Succinic Acid (0.5%) | 1.77 |
| Succinic Acid (1.0%) | 1.85 |
| Sodium Salicylate (1.0%) | 5.63 |
| Sodium Salicylate (1.0%) + Succinic Acid (0.5%) | 2.9 |
| Caprylic Acid (1.0%) | 3.93 |
| Caprylic Acid (1.0%) + Adipic Acid (0.5%) | 2.69 |
| Caprylic Acid (1.0%) + L-Malic Acid (0.5%) | 2.17 |
| Caprylic Acid (1.0%) + L-Tartaric Acid (0.5%) | 2.07 |
| Caprylic Acid (1.0%) + Unipine 90 (0.5%) | 4.06 |
| Caprylic Acid (1.0%) + Sodium Salicylate (0.5%) | 4.29 |

Example 56

Measurement of pH Values for Test Desiccants

| | pH Value |
|---|---|
| Sodium Salicylate (0.5%) | 4.48 |
| Sodium Salicylate (0.5%) + Succinic Acid (1.0%) | 2.76 |
| Sodium Salicylate (0.5%) + Succinic Acid (1.0%) + Caprylic Acid (0.5%) | 2.78 |
| Sodium Salicylate (0.5%) + Caprylic Acid (0.5%) | 4.2 |
| Succinic Acid (1.0%) + Caprylic Acid (0.5%) | 2.24 |
| Sodium Salicylate (0.5%) + Caprylic Acid (0.5%) + L-Tartaric Acid (1.0%) | 2.46 |
| Sodium Salicylate (0.5%) + Caprylic Acid (0.5%) + L-Lactic Acid (1.0%) | 2.82 |
| Sodium Salicylate (0.5%) + Capryiic Acid (0.5%) + Succinic Acid (1.0%) | 3.24 |
| Sodium Salicylate (0.5%) + Caprylic Acid (0.5%) + Succinic Acid (1.0%) | 2.32 |
| Sodium Salicylate (0.5%) + Caprylic Acid (0.5%) + L-Lactic Acid (1.0%) | 2.02 |
| Sodium Salicylate (0.5%) + Caprylic Acid (0.5%) + L-Tartaric Acid (1.0%) | 1.58 |
| Sodium Salicylate (0.5%) + Caprylic Acid (0.5%) + Unipine 90 Acid (1.0%) | 5.12 |
| Sodium Salicylate (0.5%) + Caprylic Acid (0.5%) + Adipic Acid (1.0%) | 2.78 |
| Caprylic Acid (1.0%) + Gluconic Acid (0.5%) | 2.49 |
| Caprylic Acid (1.0%) + Succinic Acid (0.5%) | 2.29 |
| Caprylic Acid (1.0%) + Beta-Alanine (0.5%) | 4.4 |
| Caprylic Acid (1.0%) | 3.85 |
| Caprylic Acid (1.0%) + L-Tartaric Acid (0.5%) | 1.76 |
| Caprylic Acid (1.0%) + L-Lactic Acid (0.5%) | 1.95 |
| L-Tartaric Acid (0.5%) | 1.72 |
| Beta-Alanine (0.5%) | 6.65 |

Example 57

Field trial comparisons of caprylic/capric and pelargonic acids on mixed weed varieties

| | Treatment | Average injury rating per plot* |
|---|---|---|
| 1 | 3% caprylic/capric | 3.95 |
| 2 | 3% caprylic/capric + 0.75% succinic acid | 4.113 |
| 3 | 3% pelargonic | 4.175 |
| 4 | 3% pelargonic + 0.75% succinic acid | 4.213 |

*A rating of 1–5 given for each of 2 plots per treatment group where 5 was complete desiccation of all plants
Plot size: 6 × 9.3 feet
Weed varieties: grasses (dominant), dandelion, pigweed, plantain and Canadian thistle
Summary: addition of succinic acid was beneficial

Example 58

Field trial comparisons of caprylic/capric and pelargonic acids on mixed weed varieties

| Treatment | | Average injury rating per plot* |
|---|---|---|
| Canadian thistle: | | |
| 1 | 3% caprylic/capric | 2.58 |
| 2 | 3% caprylic/capric + 0.75% succinic acid | 2.8 |
| 3 | 3% pelargonic | 4.03 |
| 4 | 3% pelargonic + 0.75% succinic acid | 4.35 |
| Redwood pigweed: | | |
| 1 | 4% caprylic/capric | 3.1 |
| 2 | 6% caprylic/capric | 4.55 |
| 3 | 6% pelargonic | 4.35 |

*A rating of 1–5 given for each of 2 plots per treatment group where 5 was complete desiccation of all plants
Plot size: 6 × 9.3 feet
Summary: 1) although pelargonic acid was more effective for C. Thistle, caprylic/capric performed best on redroot pigweed, 2) addition of succinic acid was effective

Example 59

Succinic Acids Potentiation of Sodium Salicylate, Testing Cotton
Treatment effect 2 days after a single, foliar application

| Treatment | Foliage Affected (%) |
|---|---|
| Succinic Acid (1.0%) | No effect |
| Succinic Acid (1.0%) + Sodium Salicylate (1.0%) | >70 |
| Sodium Salicylate (1.0%) | <70 |

Some foliage (all treatments except succinic acid, alone) beginning to drop

It will thus be seen that the objects set forth above, among those made apparent from the preceding description, are efficiently attained and, since certain changes may be made in carrying out the above methods and in the compositions set forth, without departing from the spirit and scope of the invention it is intended that all matter contained in the above description shall be interpreted as illustrative and not in a limiting sense.

It is also understood that the following claims are intended to cover all of the generic and specific features of the invention herein described and all statements of the scope of the invention which, as a matter of language might be said to fall therebetween.

Particularly, it is to be understood that in said claims, ingredients or components recited in the singular are intended to include compatible mixtures of said ingredients wherever the sense permits.

What is claimed is:

1. A herbicidal composition, comprising: an aliphatic mono-carboxylic acid in an effective amount to provide a herbicidal effect when applied to a plant; and an effective amount of an additive selected from the group consisting of succinic acid, dimethyl succinic acid, calcium succinate, magnesium succinate, diammonium succinate and ammonium succinate to increase the herbicidal effect of the composition on the plant beyond that of the composition without the additive.

2. The composition of claim 1, wherein the aliphatic mono-carboxylic acid herbicide includes at least one member selected from the group consisting of pelargonic acid, caprylic acid, caproic acid, capric acid, oleic acid, acetic acid, butyric acid, valeric acid, hexanoic acid and heptanoic acid.

3. The composition of claim 1, wherein the aliphatic mono-carboxylic acid herbicide includes at least one member selected from the group consisting of pelargonic acid, caprylic acid, caproic acid, capric acid and oleic acid.

4. The composition of claim 1, wherein the aliphatic mono-carboxylic acid herbicide includes at least one member selected from the group consisting of acetic acid, butyric acid, valeric acid, hexanoic acid and heptanoic acid.

5. The composition of claim 1, wherein the aliphatic mono-carboxylic acid herbicide comprises caprylic acid and/or pelargonic acid.

6. The composition of claim 1, wherein the additive component includes at least one additional member selected from the group consisting of, tartaric acid, citric acid, malic acid, lactic acid, adipic acid, pine oil derivatives, limonene, ammonium tartrate, ammonium chloride, ammonium sulfate and sodium salicylate.

7. The composition of claim 1, further comprising sodium salicylate.

8. The composition of claim 1, wherein the additive component further includes at least one member selected from the group consisting of tartaric acid, citric acid, malic acid, lactic acid, adipic acid and pine oil derivative, limonene and derivatives thereof.

9. The composition of claim 1, wherein the additive component further includes at least one member selected from the group consisting of ammonium tartrate, ammonium chloride and ammonium sulfate.

10. The composition of claim 1, wherein the herbicide and additive comprise 0.1 to 30% of the composition.

11. The composition of claim 1, wherein the ratio of herbicide to additive is 1:10 to 20:1.

12. The composition of claim 1, wherein the herbicide and additive comprise about 0.5 to 15% of the composition in a ratio of about 1:1 to 20:1.

13. The composition of claim 1, wherein the additive comprises succinic acid and the herbicide comprises pelargonic acid and/or caprylic acid.

14. The composition of claim 1, further comprising glufosinate-ammonium or glyphosate.

15. The composition of claim 14, wherein the additive comprises succinic acid.

16. A method of enhancing the herbicidal activity of an aliphatic mono-carboxylic acid herbicide, comprising adding to the herbicide an effective amount of an additive selected from the group consisting of succinic acid, dimethyl succinic acid, calcium succinate, magnesium succinate, diammonium succinate and ammonium succinate to increase the herbicidal activity of the herbicide.

17. The method of claim 16, wherein the additive component further includes a member selected from the group consisting of, limonene, pine oil derivatives, tartaric acid, citric acid, malic acid, lactic acid, adipic acid, ammonium tartrate, ammonium chloride and ammonium sulfate.

18. The method of claim 16, further comprising adding salicylic acid to the herbicide.

19. The method of claim 17, wherein the ratio of herbicide to additive is about 1:1 to 5:1.

20. A method of controlling plant growth, comprising: applying to a plant a herbicidally effective amount of a herbicidal composition comprising an aliphatic monocarboxylic acid to provide a herbicidal effect when applied to the plant and an effective amount of an additive selected from the group consisting of succinic acid, dimethyl succinic acid, calcium succinate, magnesium succinate, diammonium succinate and ammonium succinate to increase the herbicidal effect of the composition on the plant beyond that of the composition without the additive.

21. The method claim 20, wherein the aliphatic monocarboxylic acid herbicide includes at least one member selected from the group consisting of pelargonic acid, caprylic acid, caproic acid, capric acid, oleic acid, acetic acid, butyric acid, valeric acid, hexanoic acid and heptanoic acid and the additive includes at least one member selected from the group consisting of succinic acid, succinic acid derivatives, tartaric acid, citric acid, malic acid, lactic acid, adipic acid, pine oil derivatives, limonene, ammonium tartrate, ammonium chloride, ammonium sulfate and sodium salicylate.

22. The method of claim 20, wherein the herbicide comprises pelargonic and/or caprylic acid and the additive comprises succinic acid.

23. The method of claim 20, further comprising adding sodium salicylate to the herbicide.

24. The composition of claim 23, wherein the additive comprises succinic acid.

* * * * *